United States Patent [19]

Saito et al.

[11] 4,277,414

[45] Jul. 7, 1981

[54] PROCESS FOR PRODUCING CATALYST

[75] Inventors: Toshihiro Saito; Yukihiro Tsutsumi; Shoji Arai; Hideaki Matsunaga, all of Shin-nanyo, Japan

[73] Assignee: Toyo Soda Manufacturing Co., Ltd., Shin-nanyo, Japan

[21] Appl. No.: 109,033

[22] Filed: Jan. 2, 1980

[30] Foreign Application Priority Data

Jan. 8, 1979 [JP] Japan ................... 54-000204

[51] Int. Cl.$^3$ ............................. C07F 15/00
[52] U.S. Cl. ...................... 260/429 R; 252/431 P
[58] Field of Search ................. 260/429 R; 252/431 P

[56] References Cited

U.S. PATENT DOCUMENTS

| | | | |
|---|---|---|---|
| 3,644,446 | 2/1972 | Booth et al. | 260/429 R |
| 3,859,359 | 1/1975 | Keblip | 260/429 R X |
| 3,939,188 | 2/1976 | McVicker | 252/431 P X |
| 4,021,463 | 5/1977 | Kummer et al. | 260/429 R |

OTHER PUBLICATIONS

Budd et al., Can. J. Chem. (Canada), vol. 52, No. 5, pp. 775–781, (1974).

*Primary Examiner*—Helen M. S. Sneed
*Attorney, Agent, or Firm*—Oblon, Fisher, Spivak, McClelland & Maier

[57] ABSTRACT

A trans-[hydridocarbonyl tris(triorganic phosphine) rhodium (I)]is produced by reducing a trans-[chlorocarbonyl bis(triorganic phosphine) rhodium (I)]with a tetrahydroborate in the presence of a triorganic phosphine in a solvent by heating, an improvement characterized in that the reduction is carried out in the presence of carbon monoxide or a mixture of more than 50 vol. % of carbon monoxide and an inert gas and the reaction mixture if cooled to 0° to 30° C. in an atmosphere of carbon monoxide or a mixture of more than 50 vol. % of carbon monoxide and an inert gas and the crystal is separated. The trans-[hydridocarbonyl tris(triorganic phosphine) rhodium (I)]having high purity is obtained at high yield.

4 Claims, No Drawings

PROCESS FOR PRODUCING CATALYST

BACKGROUND OF THE INVENTION

1. Field of the Invention

The present invention relates to an improved process for producing trans-[hydridocarbonyl tris(triorganic phosphine) rhodium (I)] [RhH(CO)(PR$_3$)$_3$] (wherein R represents an organic group such as phenyl, alkyl, aryl, alkoxy and aryloxy group) by reducing trans[chlorocarbonyl bis(triorganic phosphine) rhodium (I)] [RhCl(CO)(PR$_3$)$_2$] with tetrahydroborate in the presence of a triorganic phosphine (PR$_3$) in a solvent.

2. Description of the Prior Arts

Recently, rhodium complexes especially RhH(CO)(PR$_3$)$_3$ (PR$_3$: triorganic phosphine) have been used as catalysts for a hydroformylation of an olefin, an isomerization and a hydrogenation in various fields. These compounds have been usually produced by using RhCl(CO)(PR$_3$)$_2$ as a starting material. In accordance with the conventional processes for producing RhH(CO)(PR$_3$)$_3$ from RhCl(CO)(PR$_3$)$_2$, however, a yield of the product is low and the product contains an impurity to be a low purity. It has been needed to overcome these disadvantages. Moreover, rhodium metal is remarkably expensive and accordingly, it is quite important to obtain these complexes having high purity at high yield from the economical viewpoint. It has been needed to develop an advantageous industrial process.

In the conventional process for producing RhH(CO)(PR$_3$)$_3$ from RhCl(CO)(PR$_3$)$_2$, an ethanol solution of trans-[chlorocarbonyl bis(triphenyl phosphine) rhodium (I)] [RhCl(CO)(PRh$_3$)$_2$] and triphenylphosphine (PPh$_3$) is refluxed in nitrogen gas atmosphere and then, an ethanol solution of sodium tetrahydroborate was added, to react them and the reaction mixture is separated by a hot filtration to obtain the object compound (Shin Jikken Kagaku Koza Vol. 12 Page 198 (1976) Maruzen). In accordance with the proposed process, the resulting trans-[hydridocarbonyl tris(triphenyl phosphine) rhodium (I)] [RhH(CO)(PPh$_3$)$_3$] has a low purity and contains an impurity and are not advantageous, in an industrial use as a catalyst.

In the other conventional process, an ethanol solution of rhodium (III) chloride trihydrate is added dropwise to an ethanol solution of triphenyl phosphine under refluxing the mixture and then, an aqueous solution of formaldehyde and an ethanol solution of tetrahydroborate are added to the mixture to obtain the product (J. Chem. Soc. (A) 1968 Page 2664). In accordance with the proposed process, a purity of the product is low and an yield of the product is low so that a collection step and a recovery step for rhodium are needed since rhodium is expensive. Therefore, this process is not advantageous as an industrial process.

When the product of RhH(CO)(PR$_3$)$_3$ having a low purity obtained by said process, is used with PR$_3$ and a water miscible organic solvent in a hydroformylation of an olefin, a layer of an insoluble by-product contained in the complex (an interface material) is formed between the organic solvent layer and the water layer in a step of an extraction of the reaction product with water. Therefore, an extraction in the hydroformylation is not easily attained and a loss of the expensive rhodium component is caused. When the reduction and the cooling step are carried out in a nitrogen atmosphere, an yield of the rhodium product is not high enough. The present invention has been attained by increasing the yield of the rhodium product.

SUMMARY OF THE INVENTION

It is an object of the present invention to provide a process for producing the object product of RhH(CO)(PR$_3$)$_3$ at high yield in comparison with a reaction and a treatment in nitrogen atmosphere.

The foregoing and other objects of the present invention have been attained by producing trans-[hydridocarbonyl tris(triorganic phosphine) rhodium (I)] [RhH(CO)(PR$_3$)$_3$] (wherein R represents an organic group such as phenyl, alkyl, aryl, alkoxy and aryloxy group and R can be the same or different) by reducing trans-[chlorocarbonyl bis(triorganic phosphine) rhodium (I)] [RhCl(CO)(PR$_3$)$_2$] with tetrahydroborate in the presence of a triorganic phosphine [PR$_3$] in a solvent, wherein the reduction and the following cooling treatment are carried out in the presence of carbon monoxide. It is the most important feature to carry out the reduction and the treatment in an inert atmosphere containing more than 50 vol.% of carbon monoxide.

DETAILED DESCRIPTION OF THE PREFERRED EMBODIMENTS

In accordance with the process of the invention, trans[hydridocarbonyl tris(triorganic phosphine) rhodium (I)] is produced by reducing trans-[chlorocarbonyl bis(triorganic phosphine) rhodium (I)] with tetrahydroborate in the presence of a triorganic phosphine in a solvent at an elevated temperature, in the presence of carbon monoxide and the reaction mixture is cooled to 0° to 30° C. in the presence of carbon monoxide and the crystal is separated and washed.

In the formula, suitable organic groups as R include C$_8$-C$_{18}$ alkyl groups such as octyl, decyl, dodecyl, hexadecyl and octadecyl groups; aryl groups such as phenyl, tolyl and xylyl groups; C$_8$-C$_{18}$ alkoxy groups such as octyloxy, docyloxy, dodecyloxy, hexadecyloxy and octadecyloxy groups; and aryloxy such as phenoxy group.

In the above-mentioned conventional process for reducing in a nitrogen atmosphere and separating the product by a hot filtration, the yield is upto about 90%. On the contrary, in accordance with the process of the present invention, it is possible to attain higher than 99% of the yield when the product is carefully treated.

The process of the present invention will be further described.

The first feature of the present invention is to carry out the steps from the start of the reaction to the separation of the object product of RhH(CO)(PR$_3$)$_3$ in the presence of carbon monoxide. The carbon monoxide is preferably carbon monoxide having high purity, however it is possible to incorporate an inert gas such as hydrogen, nitrogen, helium, argon etc. A ratio of the inert gas is preferably less 50% by volume.

In the reaction, a specific amount of RhCl(CO)(PR$_3$)$_2$ is suspended in a solution dissolving PR$_3$ in a solvent and a solution of tetrahydroborate in a solvent is added dropwise to the heated former solution. The solvent can be any insert solvent and preferably a lower alcohol especially ethanol.

Excess of PR$_3$ to RhCl(CO)(PR$_3$)$_2$ is used, for example, a molar ratio of PR$_3$ to RhCl(CO)(PR$_3$)$_2$ is in a range of 3 to 10. The temperature in the reaction is preferably in a range of 60° to 150° C. especially near a boiling point of a solvent when the reaction is carried out under a refluxing of the solvent.

The tetrahydroborate as a reducing agent is preferably an alkali metal salt such as sodium or potassium salt especially sodium salt. The molar ratio of the tetrahydroborate to $RhCl(CO)(PR_3)_2$ is usually in a range of 5 to 20.

It is preferable to dissolve the starting materials in the solvent in the presence of carbon monoxide. The reaction time is depending upon the heating temperature and is usually in a range of 1 to 10 hours. After the reaction, the reaction mixture is cooled to 0° to 30° C. in the presence of carbon monoxide and a crude crystal of $RhH(CO)(PR_3)_3$ is separated. The separation is usually carried out by a filtration.

The second feature of the present invention is to separate the crude crystal after cooling the reaction mixture. The steps from the reaction to the separation are usually carried out under the atmospheric pressure. If necessary, it can be higher or lower pressure.

A molar ratio of carbon monoxide to $RhH(CO)(PR_3)_3$ is usually in a range of 10 to 100.

The resulting crude crystal can be washed by a conventional solvent washing such as by an ethanol washing and a water washing, to remove a small amount of $PR_3$ and certain alkali metal components and boron components caused by the tetrahydroborate and to obtain the crystal having high purity. When the crystal contains such inorganic impurities, a clogging of a reactor may be disadvantageously caused when the product is used as a catalyst in a non-aqueous solvent.

In the washing step, it is preferable to use ethanol and water which are respectively saturated by carbon monoxide.

The crystal is dried if necessary under a reduced pressure.

In accordance with the process of the present invention, the reaction is carried out and the reaction mixture is cooled and the crystal of the object compound $RhH(CO)(PR_3)_3$ is separated in the presence of carbon monoxide whereby a side reaction can be controlled to obtain the object compound having less impurity in high yield. Since the object compound is separated after cooling the reaction mixture, the formation of the interface solid impurity caused in the hydroformylation can be prevented. Moreover, the side reaction of $PR_3$ used in excess can be decreased to be advantageous in the recovery and the reuse.

The present invention will be further illustrated by certain examples and references which are provided for purposes of illustration only and are not intended to be limiting the present invention.

EXAMPLE 1

A 1 liter four necked glass flask equipped with a inlet pipe for carbon monoxide, a thermometer, a condenser and a dropping funnel for an ethanol solution of sodium tetrahydroborate and a stirrer for electromagnetic driving (the same reactor was used in all Examples and References) was used.

In the reactor, 375 ml. of ethanol was charged and carbon monoxide was fed to purge it and then 7.5 g. of triphenyl phosphine ($PPh_3$) was added to dissolve it and 5.0 g. of trans-[chlorocarbonyl bis(triphenyl phosphine) rhodium(I)] [$RhCl(CO)(PPh_3)_2$] was added and carbon monoxide was fed to purge it. The mixture was heated under the electromagnetic stirring to reflux ethanol.

In a carbon monoxide atmosphere, a solution of 2.5 g. of $NaBH_4$ in 300 ml. of ethanol in the dropping funnel at room temperature was added dropwise into the flask to perform the reduction. After the addition, the reaction mixture was cooled to 20° C. The reaction mixture was separated by a filtration in a carbon monoxide atmosphere and the crystal was washed with ethanol and water which were respectively saturated with carbon monoxide and washed with ethanol and dried under a reduced pressure to obtain 6.64 g. of a crystal of trans-[hydridocarbonyl tris(triphenyl phosphine) rhodium (I)] [$RhH(CO)(PPh_3)_3$]. It was found that 11.2 wt.% of Rh was contained in the product by an analysis. Any sodium component and a boron component were not found by an atomic spectrography and a mass spectrometry. In order to study a presence of the above-mentioned interface solid impurity in the crystal, 0.1 g. of the crystal and 1.0 g. of $PPh_3$ were dissolved in 50 ml. of xylene in a nitrogen gas atmosphere and 30 ml. of water saturated with the carbon monoxide was added and the mixture was stirred and kept in stand-still. No solid impurity was found in the interface between the xylene layer and the water layer.

EXAMPLE 2

In accordance with the process of Example 1 except using a mixed gas of 20 vol.% of nitrogen gas and 80 vol.% of carbon monoxide gas, the reaction and the treatment were carried out to obtain 6.64 g. of a crystal. It was found that 11.2 wt.% of Rh was contained in the product by an analysis. Any sodium component and a boron component were not found. No solid impurity was found by the test for the interface solid impurity in Example 1.

REFERENCE 1

The same reaction was carried out in a nitrogen atmosphere instead of the carbon monoxide atmosphere. A solution of 5.0 g. of $RhCl(CO)(PPh_3)_2$ and 7.5 g. of $PPh_3$ in 500 ml. of ethanol was refluxed. A solution of 2.5 g. of $NaBH_4$ in 300 ml. of ethanol was added dropwise. After the reaction, the reaction mixture was separated by a hot filtration. The crystal was washed with ethanol and dried under a reduced pressure to obtain 6.0 g. of the crystal. A sodium component and a boron component were found in the crystal.

In accordance with the test of Example 1, the interface solid impurity was tested to find it in the interface between the organic layer and the water layer.

REFERENCE 2

In accordance with the process of Reference 1 except using carbon monoxide gas instead of nitrogen gas in the reaction, without using carbon monoxide in the treatment, the reaction and the treatment were carried out. A sodium component and a boron component were found by the analysis. In accordance with the test of Example 1, the interface solid impurity was tested to find it in the interface.

REFERENCE 3

In accordance with the process of Reference 2, the reaction was carried out and the crystal was washed with ethanol and water which were respectively saturated with carbon monoxide and was dried to obtain 6.10 g. of the crystal. A sodium component and a boron component were not found by an analysis. In accordance with the test of Example, the interface solid impurity was found the same as that of Reference 2.

REFERENCE 4

In accordance with the process of Example 1 except using nitrogen gas instead of carbon monoxide, in the reaction and the treatment, the reaction and the treatment were carried out to obtain 6.25 g. of the crystal. The yield was relatively low. A sodium component and a boron component were not found. The interface solid impurity was not found. The yield was remarkably lower than that of Example 1.

What is claimed is:

1. In a process for producing a trans-[hydridocarbonyl tris(triorganic phosphine) rhodium (I)] by reducing a trans-[chlorocarbonyl bis(triorganic phosphine) rhodium (I)] with a tetrahydroborate in the presence of a triorganic phosphine in a solvent by heating, the improvement characterized in that the reduction is carried out in the presence of carbon monoxide or a mixture of more than 50 vol.% of carbon monoxide and an inert gas, and the reaction mixture is cooled to 0° to 30° C. in an atmosphere of carbon monoxide or a mixture of more than 50 vol.% of carbon monoxide and an inert gas and the crystal is separated.

2. A process according to claim 1 wherein a separation of the crystal is carried out in the presence of carbon monoxide.

3. A process according to claim 1 wherein the crystal is washed with an alcohol or water which is saturated by carbon monoxide.

4. A process according to claim 1 wherein the trans-[hydridocarbonyl tris(triorganic phosphine) rhodium (I)] is a compound having the formula $$RhH(CO)(PR_3)_3$$

wherein R represents phenyl, alkyl, aryl, alkoxy, or aryloxy group.

* * * * *